United States Patent
Hoffman

[11] Patent Number: 5,931,671
[45] Date of Patent: Aug. 3, 1999

[54] DENTAL SALIVA EJECTOR TUBE ASSEMBLY

[76] Inventor: Elliott S. Hoffman, 5001 Desert Jewel Dr., Paradise Valley, Ariz. 85253

[21] Appl. No.: 09/014,838

[22] Filed: Jan. 28, 1998

[51] Int. Cl.[6] .................................................. A61C 17/06
[52] U.S. Cl. ........................... 433/91; 433/126; 433/127; 604/283; 285/320
[58] Field of Search ................................. 433/91, 93, 94, 433/95, 96, 126, 127, 129; 604/103, 283; 285/311, 312, 320

[56] References Cited

U.S. PATENT DOCUMENTS

| | | | |
|---|---|---|---|
| 2,873,528 | 2/1959 | Thompson | 433/96 |
| 3,453,735 | 7/1969 | Burt | 433/96 |
| 3,874,712 | 4/1975 | Watson | 285/311 |
| 4,083,115 | 4/1978 | McKelvey | 433/93 |
| 4,204,328 | 5/1980 | Kutner | 433/29 |
| 4,405,163 | 9/1983 | Voges et al. | 285/305 |
| 4,436,125 | 3/1984 | Blenkush | 141/330 |
| 4,822,278 | 4/1989 | Oliva et al. | 433/91 |
| 4,850,984 | 7/1989 | Harris | 604/283 |
| 4,966,551 | 10/1990 | Betush | 433/95 |
| 4,969,879 | 11/1990 | Lichte | 604/283 |
| 5,267,984 | 12/1993 | Doherty | 604/283 |
| 5,651,771 | 7/1997 | Tangherlini et al. | 604/158 |

OTHER PUBLICATIONS

Jan. 1997 Darby Dental Supply Co. Inc. Catalog Excerpt; p. 298.

*Primary Examiner*—John J. Wilson
*Attorney, Agent, or Firm*—Cahill, Sutton & Thomas, P.L.C.

[57] ABSTRACT

A socket for removably receiving an end of a dental saliva ejector tube includes a central body having a first end forming a port for being coupled to a vacuum hose. The central body includes a passage extending therethrough from the first end toward a second opposing end.

An elastic sleeve is secured over the second end of the central body for receiving the end of the dental saliva ejector tube. A pair of spreader members are secured to the elastic sleeve. A pair of levers are pivotally secured about the central body and are actuated by the user to pull the spreader members apart, thereby distending the opening of the elastic sleeve to more easily receive the dental saliva ejector tube. To prevent the dental saliva ejector tube from becoming dislodged from the socket during use, a rib may extend about the lower end of the dental saliva ejector tube.

18 Claims, 1 Drawing Sheet

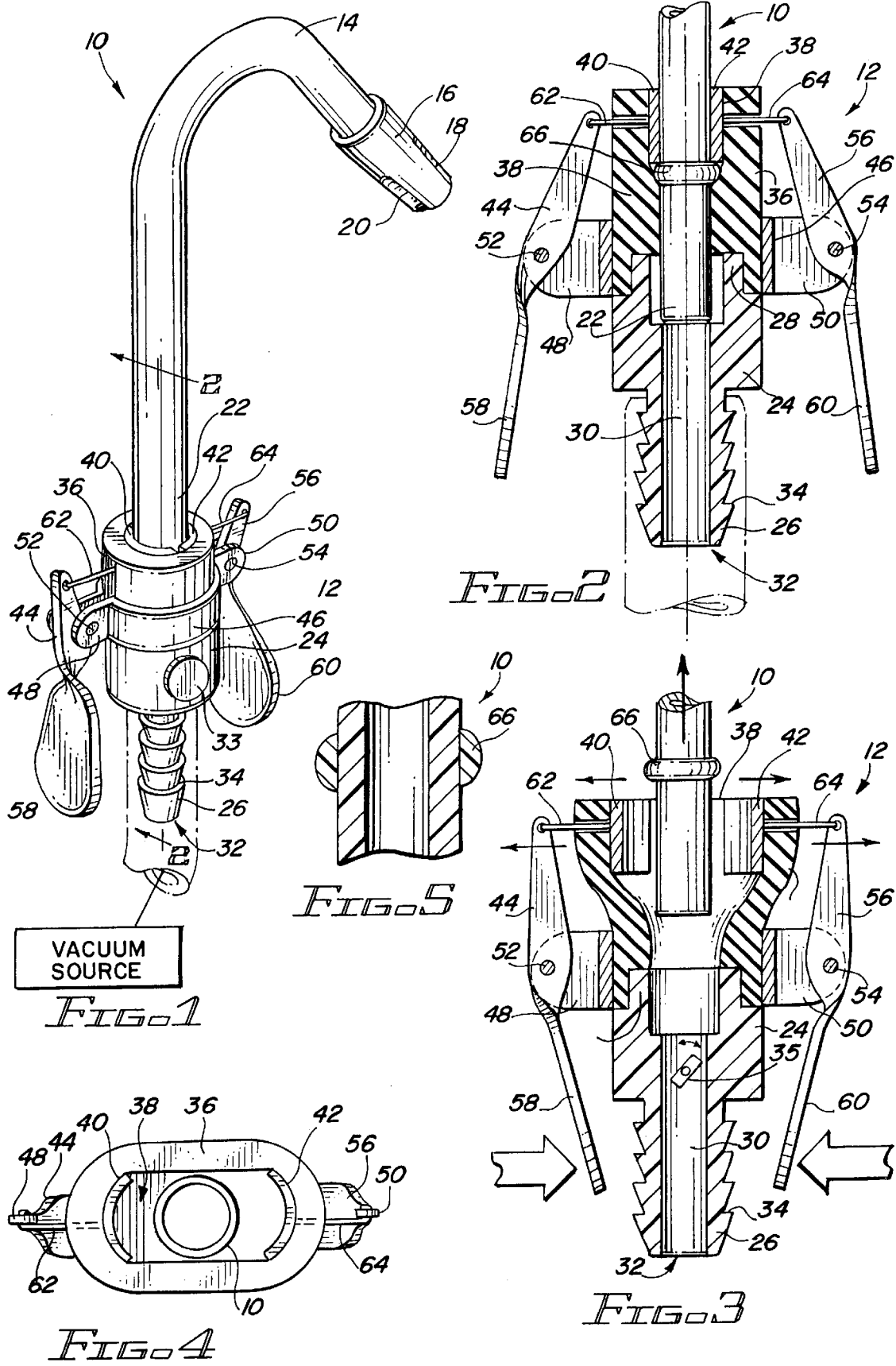

DENTAL SALIVA EJECTOR TUBE ASSEMBLY

BACKGROUND OF THE INVENTION

1. Field of the Invention

The present invention relates to dental saliva ejector tubes, and more particularly, to vacuum sockets for releasably receiving dental saliva ejector tubes for applying a source of vacuum thereto.

2. Description of the Relevant Art

In the dental profession, dentists must remove accumulated saliva, water, and other fluids from a patient's mouth, both to keep the work area clear and to avoid the need for the dental patient to swallow such fluids. Typically, the dentist makes use of a dental saliva ejector tube, along with an associated vacuum line, for such purpose. Examples of devices proposed in the past for use by dentists in removing fluids from the patient's mouth are shown in U.S. Pat. No. 2,873,528 to Thompson, U.S. Pat. No. 3,453,735 to Burt, U.S. Pat. No. 4,083,115 to McKelvey, and U.S. Pat. No. 4,204,328 to Kutner.

In one commonly used form of dental saliva ejector tube, one end of the dental saliva ejector tube is bent to form an inverted U-shape and is inserted into the patient's mouth to aspirate collected fluids. The second, or lower end, of the dental saliva ejector tube is typically inserted into a rubber fitting or grommet secured to a vacuum line. The vacuum line may include a valve for selectively closing off the vacuum. Once the dental saliva ejector tube is inserted into the rubber fitting, the dentist may, from time to time, twist or rotate the lower end of the dental saliva ejector tube within such fitting in order to change the angle at which the upper end of the dental saliva ejector tube extends from the rubber fitting. The aforementioned dental saliva ejector tubes are currently commercially available, for example, from Spencer-Meade located in Westbury, N.Y. under the model number 951-9250; these dental saliva ejector tubes are adapted to be inserted into vacuum line sockets that are commercially available by Spencer-Meade located in Westbury, N.Y. under the model number 951-9220.

The aforementioned dental saliva ejector tubes are disposable, and a fresh dental saliva ejector tube is used for each new patient. Because they are disposable, and because a dentist may use many of such dental saliva ejector tubes each day, it is desirable that the dental saliva ejector tube itself be of relatively simple and inexpensive construction. The present inventor has noted that many dentists, dental technicians, and dental assistants experience difficulty inserting the lower end of the dental saliva ejector tube. The rubber fitting or grommet has an opening that is undersized relative to the diameter of the dental saliva ejector tube in order to form a tight seal about the lower end of the dental saliva ejector tube. In addition, the dental saliva ejector tube must be somewhat pliant, rather than rigid, so that the upper half of the tube can be bent into the aforementioned inverted U-shape. The pliancy of the dental saliva ejector tube makes it more difficult to force the lower end of the dental saliva ejector tube into the opening of the rubber fitting.

A further problem experienced by dentists is that such dental saliva ejector tubes sometimes become inadvertently dislodged from the rubber fitting or grommet, as when the vacuum line becomes temporarily snagged on an object and is pulled away from the patient's mouth. In such instances, the dental saliva ejector tube must be reinserted back into the rubber fitting, thereby interrupting the procedure in which the dentist was engaged.

Accordingly, it is an object of the present invention to provide a socket of a vacuum line for removably receiving an end of a dental saliva ejector tube which simplifies the insertion of the dental saliva ejector tube into the socket.

It is another object of the present invention to provide such a vacuum line socket which allows the dental saliva ejector tube to be easily removed therefrom when a dentist has finished working upon a dental patient.

It is still another object of the present invention to provide such a vacuum line socket which allows the dental saliva ejector tube to be rotated following insertion to change the angle at which the bent upper end of the dental saliva ejector tube extends relative to the vacuum line socket.

A further object of the present invention is to provide a dental saliva ejector tube assembly including a dental saliva ejector tube and a vacuum line socket wherein the opening of the vacuum line socket can be selectively widened to facilitate insertion and/or removal of the lower end of the dental saliva ejector tube.

A still further object of the present invention is to provide such a dental saliva ejector tube assembly wherein it is less likely to inadvertently dislodge the dental saliva ejector tube from the vacuum line socket.

Yet another object of the present invention is to provide such a dental saliva ejector tube assembly having the aforementioned advantages while retaining a simple and inexpensive construction.

These and other objects of the present invention will become more apparent to those of skill in the art as the description of the present invention proceeds.

SUMMARY OF THE INVENTION

Briefly described, and in accordance with the preferred embodiments thereof, the present invention relates to a socket for removably receiving the lower end of a dental saliva ejector tube wherein the socket includes a central body having a central passage extending between first and second opposing ends thereof, the first end including a port for being coupled to a source of a vacuum, such as the end of a vacuum line hose. This port at the first end of the central body may, if desired, be barbed to insure a secure fit between such port and the vacuum line. An elastic sleeve is secured to and extends about the second end of the central body and has an opening for receiving the end of the dental saliva ejector tube. First and second spreader members are disposed proximate the opening of the sleeve for enlarging the opening of said sleeve when the first and second spreader members are moved apart from each other. At least a first lever is secured to the central body and coupled with the first spreader member; the first lever is actuated by a user for causing the first spreader member to move apart from the second spreader member for enlarging the opening of the sleeve, thereby facilitating the insertion, or removal, of the dental saliva ejector tube into, or from, the socket, respectively.

Preferably, the opening of the sleeve is circular to match the generally circular shape of the lower end of the dental saliva ejector tube, and the spreader members are arcuate to parallel the shape of the opening in the sleeve. In the preferred embodiment of the present invention, such spreader members are disposed inside the opening of the sleeve, although they can also be secured to the outer wall of the sleeve surrounding the opening of the sleeve.

The preferred embodiment of the present invention includes a second lever pivotally secured to the central body and coupled with the second spreader member. Like the first lever, the second lever is actuated by a user for causing the second spreader member to move apart from the first spreader member for enlarging the opening of the sleeve. The socket may advantageously include a bracket secured about the central body, and the first and second levers can be pivotally secured to and supported by such bracket. The first and second levers are squeezed together by the thumb and forefinger of one of the user's hands. If desired, the central body of the socket may also include a valve that can be manually operated by a user to regulate, or entirely close off, the source of vacuum, as when the dental saliva ejector tube is removed from a patient's mouth.

The aforementioned socket, when combined with a dental saliva ejector tube, provides a dental saliva ejector tube assembly that simplifies the insertion and removal of the lower end of the dental saliva ejector tube from the vacuum line socket. The above-described dental saliva ejector tube assembly can be used with commonly available dental saliva ejector tubes without requiring any modification of such tubes. If desired, however, the lower end of such saliva ejector tubes can be modified to include a generally circular rib extending thereabout. This rib extends within the elastic sleeve of the socket during use, and lessens the likelihood that the dental saliva ejector tube can become inadvertently dislodged from the vacuum line socket during use.

BRIEF DESCRIPTION OF THE DRAWINGS

FIG. 1 is a perspective view of a dental saliva ejector tube assembly in accordance with the present invention and including a dental saliva ejector tube and a mating vacuum line socket.

FIG. 2 is a cross-sectional drawing of the dental saliva ejector tube assembly shown in FIG. 1, in its rest position, i.e., when it is not being actuated by the user's thumb and forefinger.

FIG. 3 is a cross-sectional drawing similar to that of FIG. 2 but showing the levers of the vacuum line socket being depressed by the user's thumb and forefinger to facilitate removal of the dental saliva ejector tube from the vacuum line socket.

FIG. 4 is a top view of the vacuum line socket showing the enlarged opening of the elastic sleeve component of the vacuum line socket when the levers are actuated, as indicated in FIG. 3.

FIG. 5 is an enlarged sectional view of the lower end of the dental saliva ejector tube and illustrating an optional rib extending therefrom.

DETAILED DESCRIPTION OF THE PREFERRED EMBODIMENTS

A dental saliva ejector tube assembly constructed in accordance with the present invention is shown in FIG. 1, wherein reference numeral 10 generally identifies the dental saliva ejector tube and reference numeral 12 generally identifies the vacuum line socket. Ejector tube 10 is made of a pliable plastic for allowing the upper end 14 thereof to be bent into an inverted U-shape for extending over the jaw of a patient. Such ejector tubes may include a thin metal wire (not shown) embedded within the plastic and extending therealong to help keep ejector tube 10 in such bent shape, rather than returning to its original straight configuration. Upper end 14 terminates in a slotted inlet cap 16 adapted to extend within the patient's mouth; slots 18 and 20 communicate with the inner channel of ejector tube 10 and serve to suction saliva, water, and other accumulated fluids out of the patient's mouth. The lower end 22 of ejector tube 10 is circular in shape and is intended to be coupled to a source of a vacuum.

Vacuum line socket 12 is adapted to removably receive lower end 22 of dental saliva ejector tube 10. As shown best in FIGS. 2 and 3, socket 12 includes a central body 24 having a first (or lower) end 26 and a second (or upper) opposing end 28. A central passage 30 extends between first end 26 and opposing second end 28 for communicating a vacuum applied at first end 28 to second end 26. First end 26 includes a tapered port 32 for being coupled to a vacuum hose, indicated in dashed outline in FIGS. 1 and 2, which vacuum hose is coupled to a source of a vacuum and waste depository. As indicated in FIGS. 1–3, tapered port 32 may include barbs 34 for retaining tapered port 32 onto the vacuum hose. Central body 24 is preferably made of plastic or hard rubber. An optional control valve 35 (see FIG. 3) may be incorporated within central body 24 to selectively close central passage 30 and block the vacuum source from reaching opening 38; control valve 35 can be rotated manually by control knob 33 (see FIG. 1) to open or close the vacuum. Such a feature can be useful as when closing off the vacuum when the dental saliva ejector tube assembly is not in use.

The second or upper end 28 of central body 24 is in the form of a reduced diameter collar. An elastic sleeve 36, formed of pliable rubber, is secured over and around the reduced diameter collar formed at upper end 28 of central body 24 in a manner described in greater detail below. Sleeve 36 has an opening or passage 38 for receiving lower end 22 of dental saliva ejector tube 10. When at rest, in its relaxed state, the inner diameter of sleeve 36 is slightly smaller than the outer diameter of ejector tube 10 to form an airtight seal thereabout.

It will be recalled that one of the objects of the present invention is to facilitate the insertion and removal of lower end 22 of ejector tube 10 into and from socket 12. Toward such purpose, a pair of spreader members 40 and 42 are provided proximate opening 38 of sleeve 36 for enlarging opening 38 when the first and second spreader members 40 and 42 are moved apart from each other. In the preferred embodiment shown in FIGS. 1–4, first and second spreader members 40 and 42 are disposed just inside opening 38 of sleeve 36. Opening 38 is generally circular. Preferably, spreader members 40 and 42 are arcuately shaped, but the arcs thereof are defined by a somewhat larger radius than is true for the outer diameter of ejector rube 10. Accordingly, spreader members 40 and 42 tend to distort the normally circular opening 38 into a more oval shape near the upper end of sleeve 36.

As shown in FIGS. 1–3, a metal bracket 46 encircles central body 24 and the lower end of sleeve 36. Bracket 46 serves to clamp the lower end of sleeve 36 about upper end 28 of central body 24. Bracket 46 may be comprised of two metal strips, each including a semicircular middle region terminating in a pair of opposing flanges or ears 48 and 50 that extend in opposing directions away from central body 24. These two metal strips extend about opposing sides of central body 24 and sleeve 36. The two strips of metal forming bracket 46 are secured to each other by hinge pins 52 and 54 which extend through the respective ears 48 and 50, respectively, to the two metal strips.

Socket 12 further includes first and second levers 44 and 56, each of which is pivotally secured by one of hinge pins 52 and 54, respectively. Thus, hinge pins 52 and 54 and bracket 46 pivotally secure each of levers 44 and 56 to central body 24. The lower ends 58 and 60 of levers 44 and 56 are twisted through an angle of ninety degrees relative to the opposing upper ends of levers 44 and 56 to provide a control surface that can be easily depressed by a user's thumb and forefinger during use.

The upper end of first lever 44 is coupled by a thin wire 62 to the first spreader member 40. Likewise, the upper end of second lever 56 is coupled by thin wire 64 to second spreader member 42. Thin wires 62 and 64 extend through small apertures formed in sleeve 36. When levers 44 and 56 are not actuated by a user, the natural elasticity of sleeve 38 pulls spreader members 40 and 42 toward each other (prior to insertion of dental saliva ejector tube 10) or against the outer walls of the dental saliva ejector tube 10 (after insertion of such dental saliva ejector tube) as shown in FIG. 2. The portions of sleeve 36 below spreader members 40 and 42 seal about the outer walls of tube 10 to form an airtight seal thereabout.

At such times that a user desires to either insert a new ejector tube 10, or to remove an existing ejector tube 10, the user grabs the lower ends 58 and 60 of levers 44 and 56 with the users thumb and forefinger, and squeezes them together in the manner indicated in FIGS. 3 and 4. This causes the upper ends of levers 44 and 56 to move apart from each other, thereby pulling spreader members 40 and 42 apart from each other, for enlarging opening 38 of sleeve 36. The enlarged opening 38 easily permits lower end 22 of ejector tube 10 to be inserted therein, or removed therefrom.

The improved socket 12 described above can be used advantageously with conventional dental saliva ejector tubes of the type already known. However, the dental saliva ejector tube 10 can be further improved by adding a generally circular rib 66 extending about the lower end 22 of saliva ejector tube 10. Rib 66 is of somewhat greater diameter than the outer wall of ejector tube 10. During insertion of lower end 22 of ejector tube 10 into opening 38 of sleeve 36, rib 66 is positioned below spreader members 40 and 42. When levers 44 and 56 are released, spreader members 40 and 42 engage rib 66 and lessen the likelihood that dental saliva ejector tube 10 can become inadvertently dislodged from socket 12. Nonetheless, rib 66 does not preclude rotation of the lower end 22 of ejector tube 10 within socket 12, as when the dentist desires to change the angle at which upper end 14 extends.

Those skilled in the art will now appreciate that an improved dental saliva ejector tube assembly has been described which simplifies the insertion of the dental saliva ejector tube into the socket, and which allows the dental saliva ejector tube to be easily removed therefrom when a dentist has finished working upon a dental patient. The disclosed dental saliva ejector tube assembly can be used with conventional dental saliva ejector tubes and does not significantly increase the cost of current vacuum line sockets. Moreover, the optional addition of the rib to the lower end of the dental saliva ejector tube makes it less likely to inadvertently dislodge the dental saliva ejector tube from the vacuum line socket, yet still allows the dental saliva ejector tube to be rotated following insertion to change the angle at which the bent upper end of the dental saliva ejector tube extends relative to the vacuum line socket. While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A socket for removably receiving an end of a dental saliva ejector tube, said socket comprising in combination:
   a. a central body having first and second opposing ends and a central passage extending therebetween, the first end including a port for being coupled to a source of a vacuum;
   b. an elastic sleeve secured to and extending about the second end of said central body, said sleeve having an opening for receiving the end of the dental saliva ejector tube;
   c. first and second spreader members disposed proximate the opening of said sleeve for enlarging the opening of said sleeve when said first and second spreader members are moved apart from each other; and
   d. first and second levers pivotally secured to said central body, said first lever being coupled with said first spreader member, and said second lever being coupled with said second spreader member, said first and second levers being adapted to be actuated by a user for causing said first and second spreader members to move apart from each other for enlarging the opening of said sleeve.

2. The socket recited by claim 1 wherein the opening of said sleeve is circular, and wherein said spreader members are arcuate.

3. The socket recited by claim 1 wherein said spreader members are disposed inside the opening of said sleeve.

4. The socket recited by claim 1 including a bracket secured about said central body, said first lever being pivotally supported by said bracket.

5. The socket recited by claim 1 wherein the port of said central body is barbed for securely receiving a vacuum hose.

6. The socket recited by claim 1 wherein said central body includes a valve for selectively closing the central passage extending therethrough.

7. A dental saliva ejector tube assembly comprising in combination:
   a. a dental saliva ejector tube having an upper end for extending into a patient's mouth and having a lower end for coupling to a vacuum; and
   b. a socket including:
      i. a central body having first and second opposing ends and a central passage extending therebetween, the first end including a port for being coupled to a source of a vacuum;
      ii. an elastic sleeve secured to and extending about the second end of said central body, said sleeve having an opening for receiving the lower end of said dental saliva ejector tube;
      iii. first and second spreader members disposed proximate the opening of said sleeve for enlarging the opening of said sleeve when said first and second spreader members are moved apart from each other; and
      iv. a first lever pivotally secured to said central body and coupled with said first spreader member, said first lever being adapted to be actuated by a user for causing said first spreader member to move apart from said second spreader member for enlarging the opening of said sleeve in order to engage or disengage the lower end of said dental saliva ejector tube.

8. The dental saliva ejector tube assembly recited by claim 7 wherein the lower end of said saliva ejector tube is circular, wherein the opening of said sleeve is circular, and wherein said spreader members are arcuate.

9. The dental saliva ejector tube assembly recited by claim 7 wherein the lower end of said saliva ejector tube includes a generally circular rib extending thereabout to lessen the likelihood that said dental saliva ejector tube can become inadvertently dislodged from said socket.

10. The dental saliva ejector tube assembly recited by claim 7 wherein said spreader members are disposed inside the opening of said sleeve.

11. The dental saliva ejector tube assembly recited by claim 7 including a second lever pivotally secured to said central body and coupled with said second spreader member, said second lever being adapted to be actuated by a user for causing said second spreader member to move apart from said first spreader member for enlarging the opening of said sleeve.

12. The dental saliva ejector tube assembly recited by claim 7 including a bracket secured about said central body, said first lever being pivotally supported by said bracket.

13. The dental saliva ejector tube assembly recited by claim 7 wherein the port of said central body is barbed for securely receiving a vacuum hose.

14. The dental saliva ejector tube assembly recited by claim 7 wherein said central body includes a valve for selectively closing the central passage extending therethrough.

15. A socket for removably receiving an end of a tube, said socket comprising in combination:
   a. a central body having first and second opposing ends and a central passage extending therebetween, the first end including a port for being coupled to a source of a vacuum;
   b. an elastic sleeve secured to and extending about the second end of said central body, said sleeve having an opening for receiving the end of said tube;
   c. first and second spreader members disposed proximate the opening of said sleeve for enlarging the opening of said sleeve when said first and second spreader members are moved apart from each other; and
   d. first and second levers pivotally secured to said central body, said first lever being coupled with said first spreader member, and said second lever being coupled with said second spreader member, said first and second levers being adapted to be actuated by a user for causing said first and second spreader members to move apart from each other for enlarging the opening of said sleeve.

16. The socket recited by claim 15 wherein the opening of said sleeve is circular, and wherein said spreader members are arcuate.

17. The socket recited by claim 15 wherein said spreader members are disposed inside the opening of said sleeve.

18. The socket recited by claim 15 including a bracket secured about said central body, said first lever being pivotally supported by said bracket.

* * * * *